US010751243B2

(12) United States Patent
MacMahon

(10) Patent No.: US 10,751,243 B2
(45) Date of Patent: Aug. 25, 2020

(54) SCOLIOSIS OF THE MID SEGMENT OF THE THORACO LUMBAR SPINE IN ADOLESCENTS: A PROPOSED NON-OPERATIVE SOLUTION TO THE TRANSMITTER PROBLEM

(71) Applicant: Edward B. MacMahon, Middleburg, VA (US)

(72) Inventor: Edward B. MacMahon, Middleburg, VA (US)

( * ) Notice: Subject to any disclaimer, the term of this patent is extended or adjusted under 35 U.S.C. 154(b) by 474 days.

(21) Appl. No.: 15/439,337

(22) Filed: Feb. 22, 2017

(65) Prior Publication Data
US 2018/0235828 A1 Aug. 23, 2018

(51) Int. Cl.
*A61H 1/02* (2006.01)
*A61B 5/107* (2006.01)
*A61B 5/00* (2006.01)

(52) U.S. Cl.
CPC ......... *A61H 1/0222* (2013.01); *A61B 5/1071* (2013.01); *A61B 5/4561* (2013.01); *A61B 5/4836* (2013.01); *A61B 5/7275* (2013.01); *A61B 2562/0247* (2013.01); *A61H 1/0237* (2013.01); *A61H 1/0292* (2013.01); *A61H 2201/1207* (2013.01); *A61H 2203/0412* (2013.01); *A61H 2203/0431* (2013.01)

(58) Field of Classification Search
CPC .. A61H 1/0218; A61H 1/0222; A61H 1/0292; A61B 5/1071; A61B 5/4561; A61B 5/4566

USPC ...................................................... 602/32–36
See application file for complete search history.

(56) References Cited

U.S. PATENT DOCUMENTS

| | | | | |
|---|---|---|---|---|
| 2,623,518 A * | 12/1952 | Vaquette | ............ | A61H 1/0222 606/242 |
| 4,583,533 A * | 4/1986 | Goodley | ............ | A61H 1/0218 482/904 |
| 5,462,518 A * | 10/1995 | Hatley | ............ | A61F 5/024 482/124 |
| 7,715,605 B2 * | 5/2010 | Verre | ............ | G06T 7/0012 382/128 |
| 7,967,767 B2 * | 6/2011 | Ogilvie | ............ | A61F 5/024 128/869 |
| 8,784,339 B2 * | 7/2014 | Stein | ............ | A61B 34/20 600/587 |
| 2015/0257915 A1 * | 9/2015 | MacMahon | ............ | A61F 5/042 602/32 |
| 2018/0207048 A1 * | 7/2018 | Janzen | ............ | A61H 1/0292 |

* cited by examiner

*Primary Examiner* — Keri J Nelson
(74) *Attorney, Agent, or Firm* — Kimberly O Snead

(57) ABSTRACT

Non-invasive methods and systems for treating adolescent idiopathic scoliosis (AIS) that is characterized as having a Cobb angle with an apex at the mid-level of the thoraco lumbar spine are provided. The methods and systems involve the application of an overcorrecting external distractive force to the spine, the force being transmitted via actuated crutches while the patient maintains a predator crouch position that is stabilized by a support and the crutches.

6 Claims, 9 Drawing Sheets

SCOLIOSIS OF THE MID SEGMENT OF THE THORACO LUMBAR SPINE IN ADOLESCENTS: A PROPOSED NON-OPERATIVE SOLUTION TO THE TRANSMITTER PROBLEM

BACKGROUND OF THE INVENTION

Field of the Invention

The invention generally relates to improved, non-invasive methods and systems for treating the type of adolescent idiopathic scoliosis (AIS) that is characterized by a Cobb angle with an apex at the mid-level of the thoraco lumbar spine. In particular, the invention provides methods and systems for 1) obtaining the value of the force resisting correction that is secondary to the structures on the concave side of the spine being compressed by the slider-crank force vector mechanic; then 2) reversing the compression of those structures by a newly designed non-operative method of transmitting distraction forces greater than the resistance by reversing the slider-crank compression mechanics with slider-crank tension mechanics. According to the method, the patient is positioned face down in the "predator crouch" position on a support designed for double end contribution to the distraction when the core of the deformity is in the middle segment of the column.

Background

Soon after birth, a human child begins a 17 year race between two important factors. They are the time dependent anatomical development milestones which are dependent on the internal DNA and the amount of loading stresses on the body from the external environment. During this race it is essential that the DNA related anatomical development stays ahead and prepares the body to withstand the increasing loading stresses from the external environment as the child grows older.

The failure of DNA related growth of the skeleton to stay ahead of the loading stress from the environment have been identified as collapsing disorders of the skeleton during the rapid growth period. In other words, this reference separated a model of wear of a tire (osteoarthritis) from the collapse of a flat tire (collapsing disorders of the skeleton).

Collapsing disorders of the weight bearing skeleton during the 17 year race are common. For example, in the lower extremity, collapse of the roof of the acetabulum produces hip dysplasia and later osteoarthritis. Collapse of the inner or medial side of the knee causes "bow legs" whereas collapse on the outer or lateral side of the knee causes "knock knees". The obesity epidemic has increased a condition in the adolescent knee known as Blount's disease where either one or both legs become angulated from collapse of the upper medial side of the tibia. In addition, flat foot is another example of permanent collapse of the arch during the 17 year race.

At the mid-level of the spine, there is a specific anatomical design which enables the straight spine to bend to the left or right and, under normal conditions, return to verticality without difficulty. However, in some adolescents, the ability to return to straighten the spine is lost or absent, and a permanent curve develops. Small spinal curvatures are common and require only medical observation. However, scoliosis is defined as a spine whose normal lateral curvature during sideways bending has turned into an angle that is greater than 10° and with vertebral rotation. It can be classified as congenital, neuromuscular, or idiopathic, and approximately 85% of cases are idiopathic. In particular, the deformity of adolescent idiopathic scoliosis, accelerates rapidly during the adolescent growth spurt.

The degree of curvature of the spine is typically measured using the Cobb method. Using radiographic data, the measurement is made by drawing a perpendicular to a line drawn across the superior endplate of the upper-end (most tilted) vertebra and the inferior endplate of the lower-end vertebra; the angle formed by the intersection of the two perpendicular lines is the Cobb angle, which is the measure of the magnitude of the curve. (Farlex Partner Medical Dictionary© Farlex 2012) In some cases, the abnormal spinal curve is relatively minor and stable and, once present, does not change further over time and causes few problems. For example, minor scoliosis of approximately 10° (which is equally common in girls and boys) does not generally require treatment. However, with more pronounced curvature, some form of medical attention is required. If a child's spinal curve is less than 25° or if he or she is almost fully grown, the recommendation may be to monitor the curve every 6 to 12 months to be sure the curvature does not increase. However, in some children, the curve is progressive and becomes even greater with time, with severe, progressive curves occurring 5 to 10 times more frequently in girls than in boys. In these cases, the disorder can lead to visible deformity, emotional distress, and respiratory impairment from rib deformity, and treatment is required.

Unfortunately, current treatment options are very limited, inconvenient and/or highly invasive. For example, if the spinal curve is between 25° and 45° and the child is still growing, bracing may be recommended. However, bracing does not straighten an existing curve but is merely intended to prevent curvature progression. Unfortunately, the design and production of a brace for an individual is complex and costly, and braces are inconvenient for an adolescent to use. If a child's curve is greater than 45°-50°, or if bracing does not stop the curve from reaching this point, surgery is generally recommended to prevent further curve progression and to obtain some curve correction. For example, surgical treatment is used for patients whose curves are greater than 45° while still growing or greater than 50° when growth has stopped. Surgery involves the implantation of bone grafts and attachment of one or two metal rods to the spine to correct the curve and hold the spine in the corrected position. Early surgical intervention involved insertion of hooks in the upper and lower spine. But because the vertebra of the upper spine are small, the fixation of the upper hook was weak and tended to pull out. This weak link was corrected by the introduction of pedicle screws. The two hooks were replace by a single pedicle screw in each vertebra. This distributed the fixation throughout the spine and eliminated the pull-out complication. However, much more is involved surgically in the pedicle procedure. Subsequent to pedicle placement, the vertebrae of the spine segments which are involved are fused as one bone, limiting spinal movement for the remainder of the patient's life. This type of surgery is highly invasive, very costly and generally requires an extensive hospital stay followed by a long period of recuperation for the afflicted patient.

It would be of great benefit to have available methods for treating AIS characterized by a C-curve that are not invasive, are less costly, and which can fit into an adolescent's daily routine with a minimum of disruption.

SUMMARIES OF THE INVENTION

Other features and advantages of the present invention will be set forth in the description of invention that follows, and in part will be apparent from the description or may be learned by practice of the invention. The invention will be realized and attained by the systems and methods particularly pointed out in the written description and claims hereof.

The invention is based on studies by the inventor on the balancing system in the mid segments of the three top heavy vertical columns of the human musculoskeletal core. Collapse of the mid-segment of the vertebral column in adolescents converts the normal sideways curve of the spine into an angle (the Cobb angle) and is followed by a series of small compression events.

It is an object of this invention to reverse a collapse of the middle segment of the thoraco-lumbar spine, with its biomechanical adaptation to the collapse, with cycles of stretching hysteresis forces for a duration long enough to restore the Cobb angle to zero. The method involves first determining the numerical value of the stiffness of the resistance to stretching in the collapsed structures on the concave side of the curve back to their normal position. This is done with a number (e.g. three) of trial stretching of the spine with the patient face down in a "predator crouch" position. The force/displacement curves from the stretching are recorded on a computer and averaged. The stiffness is then matched to a graph showing the amount of growth remaining in the vertebral column. (Picture). A program of a Fourier series of stretching is then written to be used before bedtime to maximize use of the horizontal position when growth and remodeling of the spine occurs.

The invention thus provides improved, non-invasive methods and systems for treating one particular type of adolescent idiopathic scoliosis (AIS), namely AIS that is characterized as having an apex at the mid-level of the thoraco lumbar spine. The systems require a minimal amount of equipment, are "user friendly" to operate and are not expensive. The methods, once taught to a patient, are easily incorporated into a daily routine and can be practiced by the patient on his/her own with minimal discomfort and inconvenience, resulting in a high level of patient compliance. Briefly, a corrective force is exerted on the spine via the use of crutches, while the patient is positioned at a support in a "predator crouch" kneeling position, as described in detail below.

DETAILED DESCRIPTION

The present disclosure describes methods and systems that are designed to non-invasively and inexpensively treat a particular type of adolescent idiopathic scoliosis (AIS), namely the type that is characterized by a Cobb angle having an apex at the mid-level of the thoraco lumbar spine.

The skeletal system of hominids is characterized by having three vertical and relatively thin and top-heavy columns. They are the spine and the two lower extremities. Each column is supported on a platform: for each leg, the platform is a foot; for the spine, the platform is the pelvis. Each column, such as the spine, can be divided into 3 segments. The center segment is wider than the segments above and below, forming part of the muscular-skeletal core, and functions as a stabilizing and force transfer center. For the spine, the geometry of the stabilizing component is a "corner brace" design.

The muscular-skeletal core is divided into four integrated quadrants, namely the upper medial, upper lateral, lower medial and lower lateral quadrants. If one quadrant fails (such as occurs with scoliosis), the failure also markedly affects the other three quadrants, and this must be taken into account when treating scoliosis. With respect to conventional treatments of scoliosis, the focus on the convex side of the Cobb angle has led to an oversight regarding the importance of the contracted, shortened structure on the concave side of the curve. This contracted structure resists straightening, a phenomenon known as the "transmitter problem", and the strength of the tether that creates the transmitter problem has been measured during the placement of distracting rods at the spine during surgery.

Without being bound by theory, the present methods are based on the following: if a person can support her/his whole weight on crutches while upright and during swing-through when walking (which transmits a force to the shoulder girdle and the trunk), then, when the person is placed in a horizontal position with the pelvis stabilized, crutches can also be used to transmit a distracting force equal to the body weight through the shoulder girdles and to the trunk. A distracting force transmitted in this manner can supply the force necessary to overcome the transmitter problem, and to distract and straighten the spine. Thus, the present method addresses the transmitter problem by providing a stronger distraction force with known hysteresis effects to the shortened structures on the concave side of the Cobb angle. While the present methods do not cause straightening as quickly as surgery, they are much less invasive and much less costly. Further, the present methods usually cause straightening more rapidly than does an externally worn brace.

Figure 6:
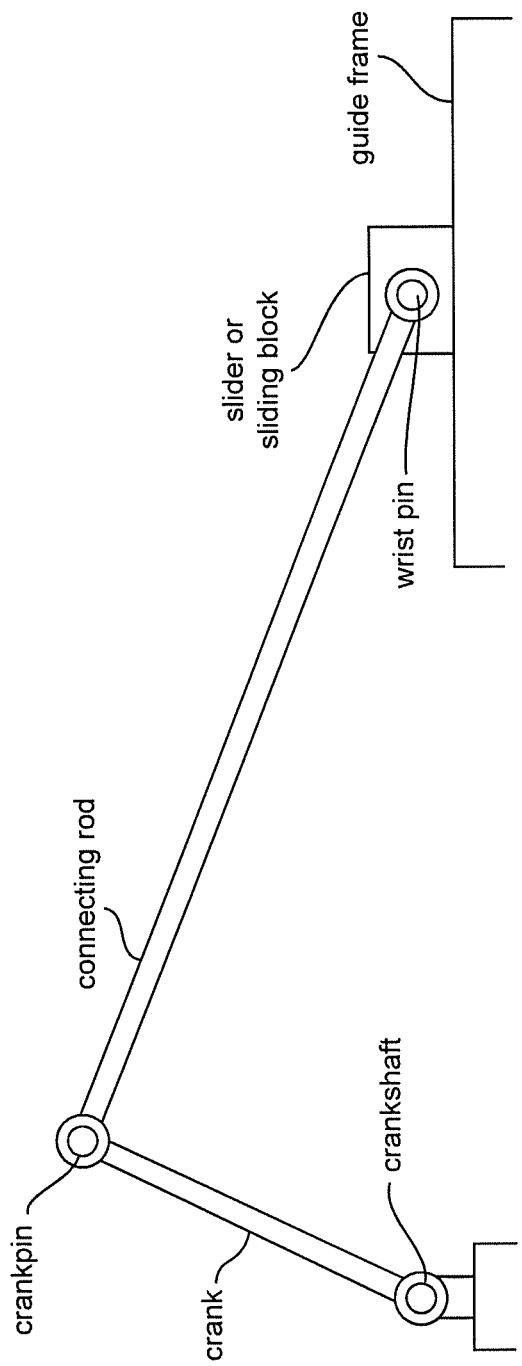
FIG. 6. Schematic representation of a slider crank mechanism.

The treatment described herein is thus based on a new model of mid segment of the thoraco-lumbar in adolescent idiopathic scoliosis, the most common class of scoliosis in children. Without being bound by theory, this new model of progression of the deformity is based on a modifications of the slider crank mechanism e.g. see FIG. 6.

The modifications are.

1. The slider corresponds to the center of mass of the upper body which moves up and down.

2. The connecting rod corresponds to the upper segment of the spine. It can be called the sliding ladder since its motion is like a ladder sliding up and down the side of a wall. Its motion is called "combined rotation and translation". See picture 3. The crankpin corresponds to the mid segment of the thoraco-lumbar spine.
4. The crankshaft which is stable corresponds to the pelvis.

The new model for reversing the "slider-crank" deformity is to reverse both ends to stretch the middle. To reverse (lift up) the collapsed slider one needs to add a horizontal beam, which corresponds to the shoulder girdles. Then, instead of using a motion akin to the strings of a Marionette mechanic as actuators to pull the slider up, crutches are use as actuators to push the slider up. This method of using two crutches reverses the translation and rotation deformity. To reverse the "crank", the pelvis can be tilted. These models and their multiple variables allow for a personalized reversal of the deformity which is generally more rapid than bracing but is generally slower but much less invasive than surgery.

Figure 7:
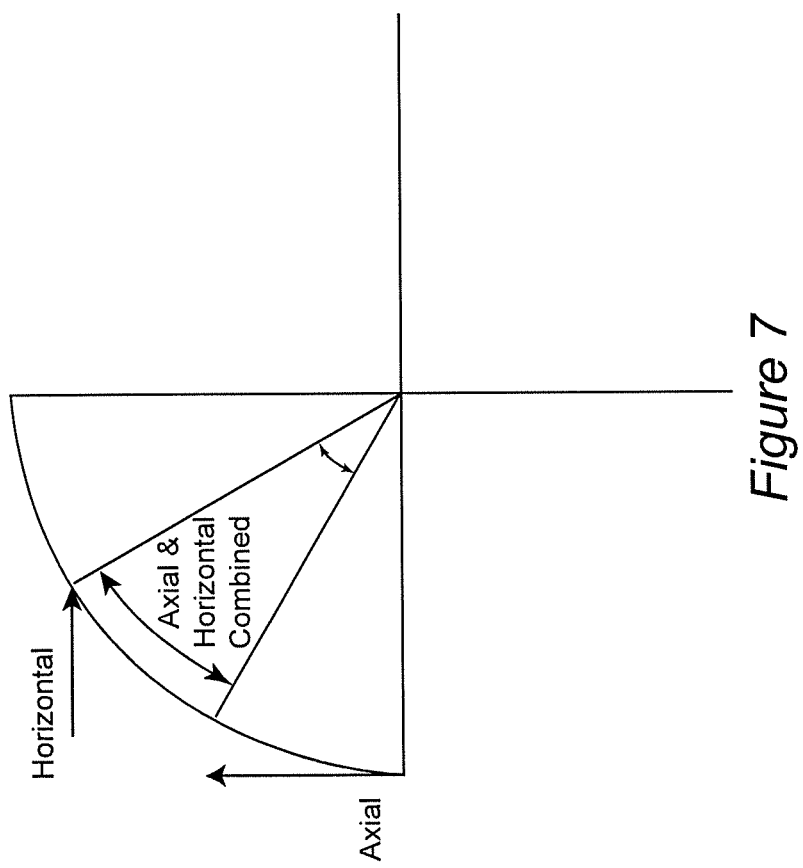
FIG. 7. Graph showing axial, horizontal and axial plus horizontal force direction.

Those of skill in the art will recognize that the apex of mid segment adolescent scoliosis progresses in an "orbit" to 90 degrees in 3 steps: from neutral to 30 degrees it is mainly horizontal; from 30 degrees to 60 degrees it is a combination of vertical and horizontal; and from 60 degrees to 90 degrees it is mainly vertical. The device described herein is designed to reverse these steps from 90 degrees to 60 degrees by exerting a (primarily) axial distraction; from 60 degrees to 30 degrees by exerting a combination of axial distraction and horizontal rotation; and finally from 30 degrees to zero by exerting a (primarily) horizontal force (FIG. 7). In other words it solves the problem of reversing the deformity using just one integrated method.

Definitions/Explanations

Actuator:

An actuator is a component of a machine that is responsible for moving or controlling a mechanism or system. An actuator requires a control signal and a source of energy. The control signal is relatively low energy and may be electric voltage or current, pneumatic or hydraulic pressure, or even human power. The supplied main energy source may be electric current, hydraulic fluid pressure, or pneumatic pressure. When the control signal is received, the actuator responds by converting the energy into mechanical motion. The control system can be simple (a fixed mechanical or electronic system), software-based, etc.

Biomechanical Adaptation:

Biomechanical adaptation to training refers to the ability of the body to refers to the process of the body becoming accustomed to, and changing in response to, a particular exercise or training program through repeated exposure.

C-Curve

A C-curve is usually referred to when one leg is longer than the other. It is also used to refer to a long curve when one bends the spine to the left of right. When a spine "buckles" or "collapses", the curve changes into an angle, the Cobb angle (see FIG. 1). However, a Cobb angle can be simulated by tilting the pelvis down on one side clockwise and tilting the shoulders counter-clockwise (or the reverse, i.e. the pelvis is tilted counter-clockwise and the shoulder are tilted clockwise). This causes a bending of the spine at the mid-level (mid-segment, mid-musculoskeletal core). The bend becomes pathological when is becomes fixed in one direction and does not require tilting of the pelvis to attain the bend. The mid-segment is also the widest so it can be the apex of bending from side to side and can safely bend back in an opposite direction. This property of the mid-segment is exploited to safely correct a fixed bend.

Long axis of the body: the imaginary straight line in the median plane that nearly intersects the center of all transverse planes through the body, running from the apex of the cranium through the center of the perineum and continuing between the lower limbs, parallel to and equidistant from the long axes of the limbs.

Mid-Segment Scoliosis

Mid-segment scoliosis refers to the change in a normal top heavy vertical spine when it buckles in the mid-level from the weight about the mid-level. The buckling converts the normal curve produced while bending to the left or right into an angle called the Cobb angle, defined elsewhere herein. The Cobb angle is similar to the Coventry angle of the knee is "bow legs" and "knock knees".

Shoulder Girdle:

The shoulder girdle or pectoral girdle is the set of bones which connects the arm to the axial skeleton on each side. In humans it consists of the clavicle and scapula.

Slider-Crank Mechanism:

The Slider-crank mechanism transforms rotational motion into translational motion by means of a rotating driving beam, a connection rod and a sliding body.

Thoraco-Lumber Spine and Cores:

Each of the three vertical top heavy columns of humans (the thoraco-lumber vertebral column or spine, and two legs) is divided into three segments: upper, middle and lower. The middle segment of each column is the widest segment and is called the musculo-skeletal core. In the lower extremities, the knee joint is at the center of the core.

The three segments of the thoraco-lumber spine are supported on the pelvic platform. The upper segment is the vertebrae T1-T7 with three associated true ribs, meaning they are directly attached to the sternum. The T7 and T8 ribs are the longest in the body. The remaining ribs (T8-T12) are divided into two groups the false ribs are T8-T10 (named "false" because they are not directly attached to the sternum). The last two ribs, T11 and T12, are called the "floating" ribs because they have no distal attachment. In the thoraco-lumber vertebral column, the core is the area of the false ribs (T8-T12).

In addition, each of the three cores is divided into four quadrants, two upper and two lower. The medial and lateral upper quadrants in the vertebral column are the ribs T8, T9 and T10. The lower quadrants are the floating ribs T11 and T12. In the lower extremities, the medial and lateral quadrants of the upper part are the medial and lateral parts of the lower femur. In the lower half, they are in the upper part of the tibia.

Figure 1:
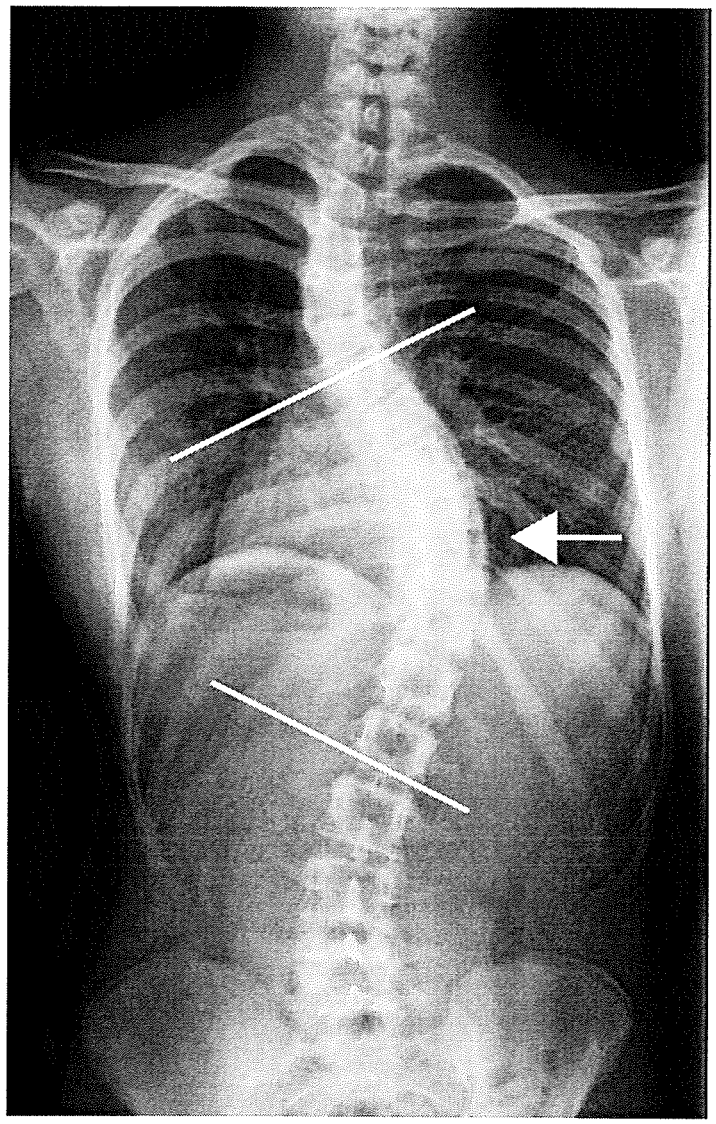
FIG. 1. Schematic representation of a patient positioned to carry out the method described herein.

The importance of the cores is that their function is to act as stabilizers and force transfer centers for the segments above and below them. Therefore, when a quadrant in the mid-vertebral segment (core) collapses, the patient develops scoliosis. In scoliosis, the floating ribs on the concave side of the Cobb angle are the first to collapse from the weight above them. They correspond to the upper medial plateau of the tibia which first collapses in the type of bow legs called Blount's disease. For a patient with scoliosis, the center of the Cobb angle is located in the collapsed quadrant. For the same reason, when a quadrant of the knee core collapses, the patient develops a bow leg or knock knee, depending on whether the quadrant was medial or lateral. FIG. 1 shows an x-ray of a scoliotic spine and depicts angulation due to the collapse of one quadrant.

Wolff s Law:

Wolff s law, developed by the German anatomist and surgeon Julius Wolff (1836-1902) in the 19th century, states that bone in a healthy person or animal will adapt to the loads under which it is placed. If loading on a particular bone increases, the bone will remodel itself over time to become stronger to resist that sort of loading. The internal architecture of the trabeculae undergoes adaptive changes, followed by secondary changes to the external cortical portion of the bone, perhaps becoming thicker as a result.

Figure 2A:
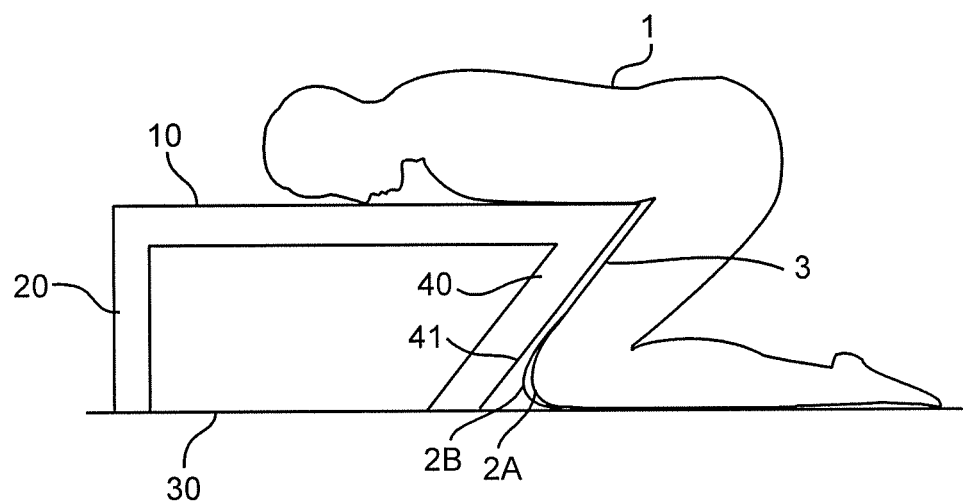
FIG. 2A-D. Schematic representations of patient positioned on a support. A, side view of patient in predator crouch position; B, subject's knees aligned by a tilted surface; C, subjects knees aligned by a stepped surface; D, subject's knees aligned using an addition support.
Figure 2B:
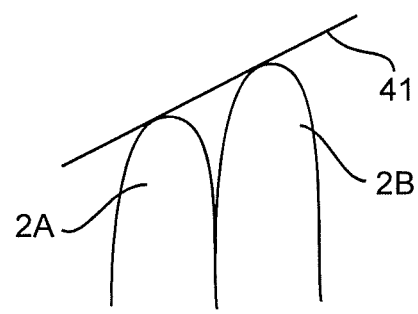
Figure 2C:
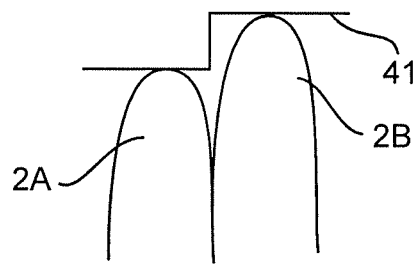
Figure 2D:
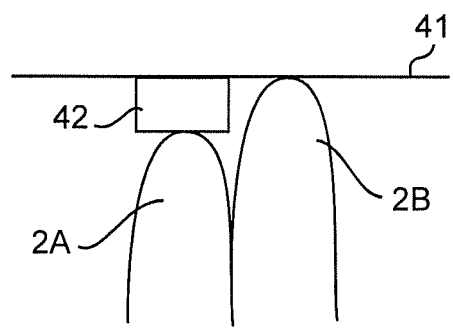

The methods and systems described herein are designed to apply an external corrective force to the spine in order to treat AIS. By "force" we mean an interaction that, when unopposed, changes the motion of an object, including to begin moving from a state of rest. A force has both magnitude and direction, making it a vector quantity. Force is measured in the SI unit of newtons and represented by the symbol F. The force that is applied is greater than that which is need to simply place the spine in a straightened position. Rather, the force over-corrects for the curve stiffness so that the natural recoil or reaction force of the spine, which will tend to "snap back" into the original position, is overcome. Eventually, upon withdrawal of the force, the spine will "relax" into a position that is near or nearer to straight, the curve having been removed. In the practice of the invention, the force is generated and transmitted to the patient him/herself via the use of crutches (or a similar type of support) equipped with an actuator, while the patient is positioned face down on a support in a "predator crouch" position with the pelvis tilted at a predetermined angle and stabilized The method is practiced as follows: while kneeling, the patient leans forward from the hips onto a support adapted to permit the subject to adopt a "predator crouch position", i.e. the knees are flexed while the upper body of the subject (from and including the head to the pelvis), is horizontally supported face downward on an upper horizontal surface of the support. An example of this positioning is shown schematically in FIG. 2a, which shows a lateral side view of subject 1 leaning face down and forward from the hips, onto upper horizontal surface 10 of support 20, which is stably positioned on floor 30. Support 20 is designed with an angled member 40 which extends back under horizontal surface 10. Thighs 3 of subject 1 press up against exterior surface 41 of angled member 40, and knees 2a and 2b of subject 1 are accommodated within the angular space created between angled member 40 and floor 30. Significantly, as shown in FIG. 2a, one of knees 2a and 2b (in FIG. 2a, knee 2b) extends further under support 40 than the other. The differential placement of the knees causes the pelvis of the subject to tilt at a predetermined angle (which may range from about 5° to 75°, e.g. about 5, 10, 15, 20, 25, 30, 35, 40, 45, 50, 55, 60, 65, 70 or 75°), and the pelvis is stabilized in this position during treatment. In order to support the positions of the knees, exterior surface 41 may be angled (as shown in the top view 2b), or "stepped" (either permanently or adjustably) as shown in FIG. 2c, or an additional support 42 (e.g. a permanent or detachable member such as a cushion, a wooden, plastic or foam block, etc.) may be inserted in front of the knee that is further back, as shown in FIG. 2d. Those of skill in the art will recognize that the depictions in FIGS. 2a-d are illustrative only, and that for some patients, in order to attain the correct pelvic tilt, the left leg would be forward, and the relative distances of the two knees with respect to each other and exterior surface 41 may differ.

While in this position, the patient places no or very limited weight on the feet. In this position, the pelvis and femurs are stabilized in a substantially fixed position as one solid unit (the "femoral-pelvis unit"), giving the subject a firm anchor. In addition, the shoulder girdle and the upper thorax are also stabilized as a unit (the "shoulder girdle-upper thorax unit"). This face down position takes the gravity force of the trunk off the spine, thereby permitting the stabilized shoulder girdle-upper thorax unit and spine to move relatively freely in unison in response to a distractive force.

The distractive force is exerted via crutches. The patient assumes the predator crouch position while holding two crutches in a substantially conventional manner, i.e. the crutches are engaged, one on each side of the subject, such that the top, horizontal portion of each crutch is supported by the V-shaped shoulder depressor (girdle) muscles which act as a "sling" connecting the upper humerus to the thoracic cage. This muscle sling can support the full or almost the full body weight of a subject during the swing through when using a crutch, and thus provides a rigid proximal anchor for distraction of the apex of the Cobb angle in the middle of the spine. In some aspects, subjects that are selected for treatment using the methods described herein are pre-trained, prior to being treated, to teach them the swing through gait, and to strengthen the shoulder girdle muscles (e.g. using weights), to insure that the muscles have sufficient endurance to permit the practice of the method. For example, when positioned for a swing through gait, the patient is asked to exert weight on two bathroom scales using the crutches (one crutch per scale). In general, the patient should be able to exert about 20 pounds or more of weight per crutch, i.e. a total of 40 pounds of axial distraction, in cycles of about 2 minutes, as tolerated, before being treated as described herein.

Figure 3:
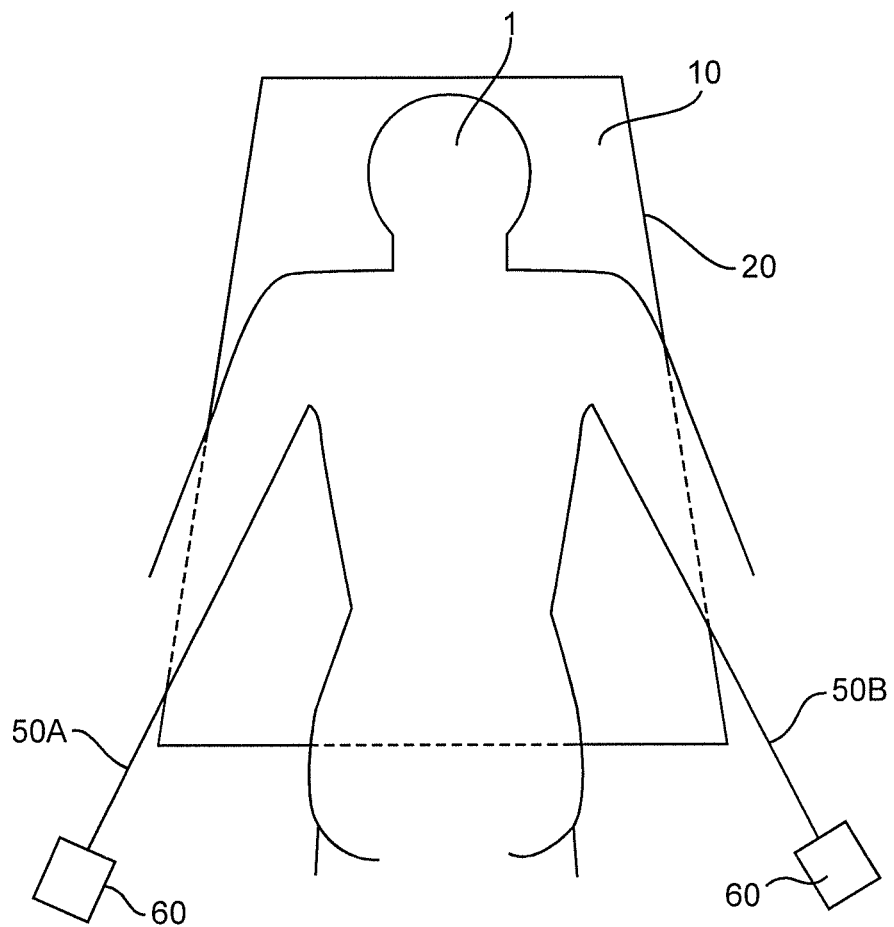
FIG. 3. Schematic representation of a top view looking down at a patient positioned face downward on a support, in order to carry out the method described herein.

A basis of the present treatment is that crutches in a swing through gait transmit to the thorax a force as high or even higher than the distraction forces recorded during corrective surgery for scoliosis, e.g. with Harrington rods. This or a similar force is introduced to the spinal column of a subject during a distraction treatment of the present invention because the subject is positioned so as to have a fixed pelvic anchor with a tilt while in the predator crouch position. During the distraction treatment, the elbow is held straight and is thus braced and stabilized. These features are illustrated schematically in FIG. 3, which shows a top view from the rear and looking toward subject 1 lying face down on upper horizontal surface 10 of support 20 with crutches 50a and 50b in position. Actuator 60 is also shown at a distal end, in this case, of both crutches 50a and 50b. While in the predator crouch position, one knee of the subject is extended further under the support than the other, causing the pelvis to tilt. This is illustrated schematically in FIGS. 4a and b, each of which shows a top view of the subjects right knee 2a and left knee 2b in phantom as they are extended under support 20 while the subject is in a predator crouch position. As can be seen, right leg 200 is further under support 20 causing a shift in the position of the pelvis, i.e. a tilt in pelvis angle A1 in the direction shown by the arrow within angle A1. In the schematic representation of FIGS. 4a and 4b, the direction of the tilt is away from the concave side of the curve due to the differential placement of the knees. In other words, the pelvic platform is tilted in the opposite direction to the tilt that is introduced into the upper segment during a treatment session (see below)

At least one, possibly both, of the crutches that is used in the practice of the present invention is equipped with an actuator (60 in FIG. 3) which is in turn electrically connected to and controlled by e.g. a software program run by a computer system. The actuator is located at a distal end of the crutch and is in contact with the flooring on which the support is set. The initial patient positioning results in establishment of a stable pathway for transmitting a controlled distraction hysteresis force from the computer-controlled actuators to the shoulder girdles and the upper thorax.

Thus, during treatment, upon receiving an electrical signal from an electrical controller which may be operated by a suitable software program, the actuator exerts a suitable pre-determined distractive force that is transmitted up the pathway beginning at the actuator and extending through the hand grips of the crutches, through the forearm and the braced straight elbow, through the upper humerus and to the shoulder girdle of the subject. The distraction force is exerted upward by only one crutch while the other crutch is firmly braced with its distal end on the flooring to further stabilize and prevent shifting of the torso as a whole during a treatment. This results in a rotation of the shoulder girdle-upper thorax unit with respect to the long axis of the body and in a plane parallel to the upper surface of the support, and a concomitant "tugging", pulling or bending of the spine. The force is applied from the thorax and its attachment to the upper part of the middle segment to the attachment of the lower part of the middle segment, which is anchored through the lower segment to the pelvis platform, thereby stretching the shortened resisting structures on the concave side of the C curve and forcing the spine to straighten. The action is similar to straightening a curled string by pulling both ends of the string.

Figure 4A:
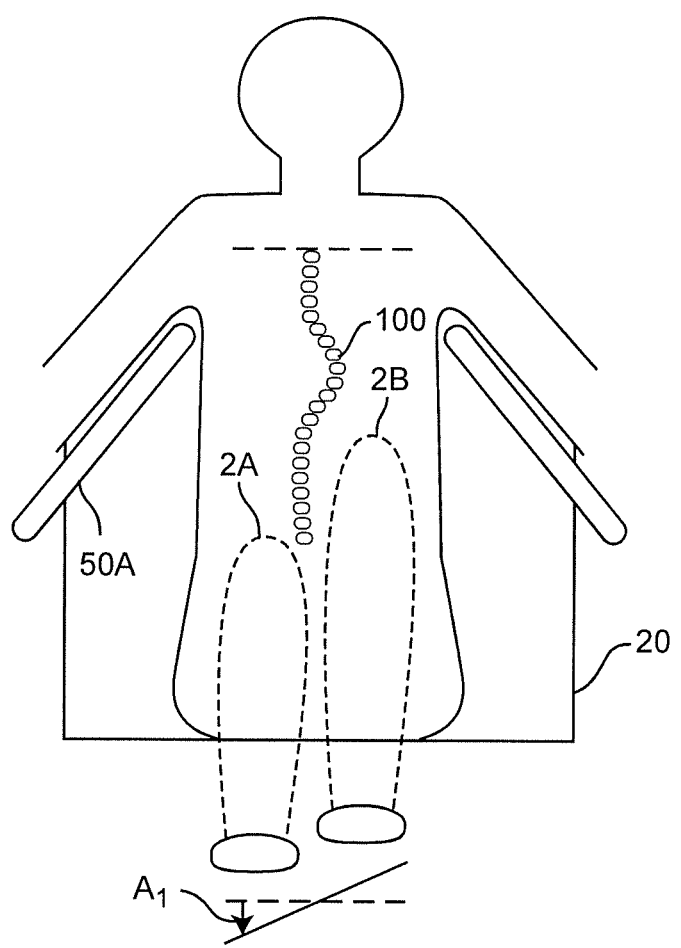
FIGS. 4A and B. Schematic representation of a subject during a treatment session. A, subject positioned before application of distraction force; B, subject during application of distraction force.
Figure 4B:
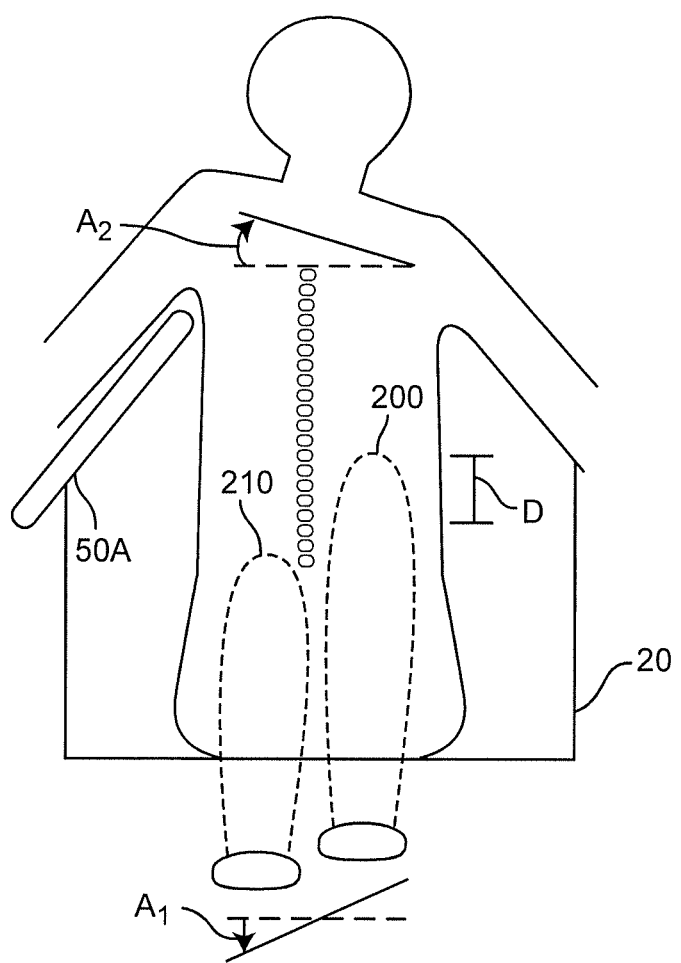

The distraction movement that occurs during a treatment session is illustrated schematically in FIGS. 4A and B. FIG. 4A shows the upper torso of a subject with Cobb angle 100 prior application of a distraction force. Knees 2a and 2b are positioned as shown, causing the pelvic floor to tilt by angle A1. The degree of the desired tilt is predetermined by taking into account, for example, the degree and location of spinal angulation, the degree of spinal stiffness, the degree of rotation of the upper segment of the deformed vertebral column, the degree of rotation of a lower segment of the deformed vertebral column, etc., together with the amount of force that must be generated to straighten the spine. The function of the tilted pelvis is to act as a distal anchor for the distraction force while at the same time rotating the distal segment in a direction that is opposite to the rotation of the upper segment, which ensues when the distractive force is applied, and straightens the spine. Application of the force is illustrated in FIG. 4b. Application of a distraction force via crutch 50a causes the upper torso to rotate (e.g. by angle A2) in a direction that is opposite to the direction of rotation of the pelvis, thereby lengthening the spine and reducing or eliminating the spinal curvature, i.e. the Cobb angle is reduced to zero.

The force that is applied during a treatment session is generally greater than that which is required to "straighten" the spine. In other words, the amount of force that is used overcorrects for the curvature. This is to prevent the spine from relaxing back to the original position, or to a position that is only partially corrected, after treatment. However, the required force is not necessarily exerted all at once in a single session; rather, what is needed is repetition to gradually loosen and stretch the shortened resisting structures on the concave side of the C curve, which allows the spine to eventually adopt a normal (or near normal) straightened aspect. Thus, the straightening occurs incrementally. Further, the amount of force required to push the spine toward the desired endpoint may be adjusted as necessary over the course of treatment, e.g. as the patient's progress is monitored.

The amount of force (including magnitude and direction) that is necessary to correct the spinal curvature is determined by one or more of several known methods of assessing spinal curvature, taking into account, for example, the degree of curvature, the rotation of the spine, the stiffness or flexibility of the spine, etc. In general, the force that is applied is calculated so as to overcorrect for the curvature until a desired level of straightening is achieved. Typically, the amount of force that should be applied is calculated as follows: First, the Cobb angle is measured and compared to a graph indicating the amount of residual growth of the thoracic spine. Next, the stiffness of the resistance to stretching. This is done by placing the patient on a table or support in the predator crouch position as described herein, and performing three trial distractions using both actuators. The results are averaged to give the slope of the force displacement. A decision to recommend surgery or a course of distraction as described herein is based on the three variables Cobb angle, remaining growth and stiffness of the resistance.

In general, the force is applied to the spine by the patient for a period of time of about 20-30 minutes (e.g. about 15, 20, 25 or 30 minutes) per session. In some aspects, the force is applied during the entire time. In other aspects, the force is applied for several shorter periods of time, e.g. ranging from about 5 to about 15 minutes (e.g. about 5, 10, or 15 minutes), with short breaks (e.g. 2-3 minutes) in between.

In general, therapy sessions are engaged in at least once a day, usually just before bedtime. Thus, the lengthening is remodeled during the nighttime when gravity is absent and axial growth occurs. However, in some cases, the sessions may be scheduled less frequently (e.g. every other day) or more frequently (e.g. twice a day, such as in the morning and in the evening), etc. The duration of treatment varies from patient to patient, but is generally for at least about 10 weeks, with e.g. daily telemedicine check-ups and e.g. bi-weekly check-ups at a doctor's office. In addition, those of skill in the art will recognize that the details of the treatment (e.g. the amount of force, the frequency and length of therapy, etc.) may vary from patient to patient, and may change for a given patient over time, e.g. as progress is made with straightening the spine, less force and/or shorted treatment sessions may be required.

In addition, the treatment may include a prescribed series of exercises several times during the day (e.g. 2-10 times) to prevent gravitational force from undoing the benefits of nighttime stretching. Basically, the patient, in a standing position, tilts the pelvis and the shoulders is the directions that are adopted during treatment sessions and holds the position for at least about 30 seconds, doing several (e.g. 5-10) repetitions. This action bends the spine in the direction that is targeted during treatment sessions, albeit with less force.

The goal of treatments described herein is to reduce the Cobb angel to zero, i.e., to completely remove the spinal curve. However, those of skill in the art will recognize that much benefit can accrue even if this is not possible, e.g. if the stiffness is too great or too little growth potential remains. In such cases, it is still possible to prevent further progression of curvature (i.e. to stabilize the curve) and if possible, to reverse angulation to a suitable level that does not interfere with the health and well-being of the subject. For example, the angle may be reduced to about 10° or less.

The crutches that are used in the practice of the invention are of any suitable sort, e.g. conventional "Y" shaped crutches, "L" shaped crutches, etc., or similar supports that are custom made. The crutches may be made of wood, aluminum, or any other suitable material. The crutches comprise an upper horizontal segment designed to fit into the armpit of the user, and a handgrip onto which the user can exert an upward force toward the armpit. Exemplary crutches are described, for example, in issued U.S. Pat. Nos.

8,720,458; 9,289,346; 9,326,572; and 9,364,384; and published US patent applications 20160287464, 20160310345 and 20160249715, the complete contents of each of which are hereby incorporated by reference in entirety. Any type of "crutch" or similar support may be used, so long as it is fashioned with a hand grip and an upper horizontal section that fits in the armpit of the user, and permits the upward force to be transmitted as described herein. Each crutch is equipped with an actuator which drives the upward motion of at least one of the two crutches. Many commercially available actuators of this type are known and readily available. In order to practice the methods described herein, the factors described above are measured (e.g. Cobb angle, stiffness, etc.) and the amount of force necessary to reverse the Cobb angle is calculated. A patient-specific computer program is then written to direct the actuators to exert a particular suitable level of force on one crutch or the other at predetermined intervals.

When practicing the methods described herein, the subject assumes a kneeling predator crouch position while leaning forward and face down onto a support so that the weight of the upper body of the subject (e.g. roughly from the hips/pelvis upwards, and including the pelvis) contacts and is supported by an upper surface of the support. The support (e.g. a bench) that is utilized in the practice of the invention is made or adjusted to comfortably accommodate the patient according to height, weight, etc. The height and width of the support is or is adjusted to allow the subject to assume the predator crouch position while retaining the crutches in place in a typical way (i.e. with the uppermost horizontal components fitted into the armpits and the hands gripping the hand grips). In some aspects, the subject while so positioned turns his or her head to the side in order to easily breath. In other aspects, the head of the subject is supported but the face is not occluded e.g. by providing an adjustable, movable portion that slidably fits or is otherwise attached to one end of the support (the end that receives that subject's head). This upper, movable portion receives the forehead of the subject but is "cut away" or otherwise designed so as not to occlude the nose, eyes and mouth of the subject. Alternatively, a hole that accommodates the face may be located in the support directly beneath the head; or various types of cushioning (e.g. to support the neck) may be present to promote the comfort of the subject during treatment. The support itself may be in the form of a bench (e.g. similar to a weight lifting bench, an examination table or a massage table) and typically includes cushioning on the upper horizontal surface for the comfort of the subject.

As described above and shown in FIG. 2A, the support may comprise a slanted or angled member that extends from one edge of the support (the edge against which the subject's pelvis is positioned) and back under the support, thereby forming an angle with the horizontal surface of the support. The space formed between the angled member and the floor accommodates the knees of the subject during treatment. The angled member may be an integral part of the support, or may be insertable into the support when in use and removable when not in use. The size of the angle made by the angled member varies from subject to subject, and is generally e.g. smaller for younger or diminutively proportioned subjects, and greater for larger or more robustly proportioned subjects. To this end, the supports that are used in the practice of the invention may be tailor made to the specifications that suit a particular patient (e.g. height, width, size of angle, etc.), or may be adjustable so that many sizes of patients can use the support, or so that a single patient can use the same support over a number of years while growing, etc.

In addition, the support may be adjustable with respect to the "tilt" of the upper surface of the support, i.e. the surface of the support that is in direct contact with the upper body of the subject. This upper section of the support is generally substantially planar, and the plane may be tipped or tilted in any direction as necessary in order to contribute to generating the correct angle for application of a corrective force, and/or for the comfort of the patient. For example, the support may be rotated to the left or right along its long axis. The system of the invention is a computerized system that comprises at least the following components: a support for supporting a subject who is practicing the method disclosed herein; two crutches, each of which is equipped with an actuator; and a computer comprising e.g. an input for receiving force information (data) that is transmitted electronically from (outputted from) at least one of the actuators, a data processor to process data received through the input, a display unit to display the force data in a format that is readable and/or visible to the patient before, during and/or after use of the system, and a control module configured to coordinate all system components. In some aspects, the data output is real time so that the patient can monitor the force during the therapy session. therapy schedules, progress reports, etc.

The system components generally also include a computer readable medium comprising non-transitory instructions that when executed cause a processor to perform the an analysis of data relevant to spinal curvature that is inputted by a user, analyze the data, and calculate and then output e.g. the amount of force (including magnitude and angle) that is required to correct a spinal curvature. The input may include, for example, measurements previously obtained for the subject such as the degree and convexity of the scoliotic curve; the degree of rotation of the spine in the affected area; spinal flexibility; height, weight, age and gender of the patient; skeletal maturity, e.g. using iliac crests as an index; etc. The software program may be capable of monitoring and tracking patient therapy sessions (both during a given sessions as well as the cumulative historical data from all sessions, etc.), notifying the patient (and/or a supervising physician or therapist) if a patient is not compliant (e.g. if therapy sessions are missed), reminding the patient when progress assessments are due, etc. In addition, the computerized system may include a voice module which communicates information audibly to the user, as well as means for displaying and/or printing out reports of data.

Figure 5:
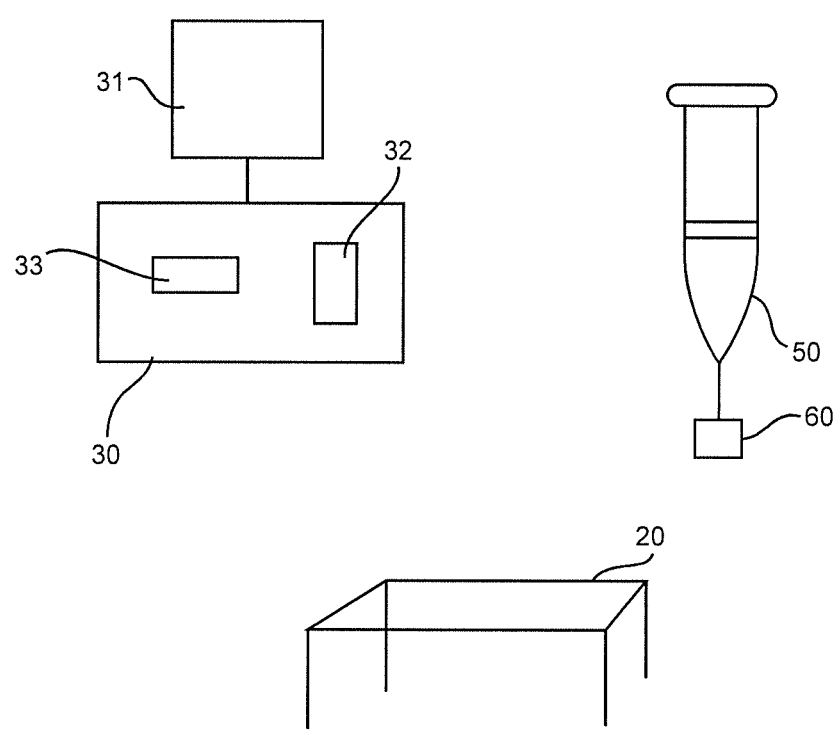
FIG. 5. Schematic representation of a system for performing the methods described herein.

An exemplary system is depicted schematically in FIG. 5, which shows computer 30, display 31, controller 32, processor 33, crutch 50 with actuator 60 installed thereon, and support 2.

While exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise. Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

In a pre-high school physical, the pediatrician of a 13-year old girl notices a hump in her back while listening to her lungs. A follow-up X-ray shows a scoliosis deformity of her thoracic spine, and the apex and the Cobb angle of the deformity are determined. The pediatrician, referring to the 2005 AAOS treatment guidelines, refers the parents to a surgeon and to a bracemaker for options. The surgeon and the bracemaker are both willing to undertake treatment, each according to his/her specialty, and each explains what is involved in terms of discomfort, cost, etc. The surgeon states that in a d-hour procedure their daughter's spine will be straightened permanently. The bracemaker states that if their daughter wears a brace for 23 hours a day for 3 years, the spine will be somewhat improved.

The parents consulted a practitioner of the present invention and were told that the present treatment is based on models of normal growth of the three, top heavy columns of the trunk, in which the middle segment is a potential "weak link" in the balancing and stabilizing system, and how the weak link can fail by verticals buckling, resulting in scoliosis. The present methods of treatment are also described in which a computer controlled collateral distraction force is applied daily to reverse spinal angulation over a period of weeks or a few months. The treatment sessions, which are done at home, require some basic initial strength training followed by nightly treatment sessions before bedtime, with each session lasting about 20-30 minutes, In addition, some straightforward daily exercises are required during the course of treatment.

The girl is treated using the methods described herein, and the Cobb angle is reduced to zero over a period of 10 weeks, without any additional intervention.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method of non-invasively treating adolescent idiopathic scoliosis (AIS) characterized as having a deformed vertebral column with Cobb angle having an apex at the mid-segment of the thoraco lumbar spine, in a subject in need hereof, comprising
   i) measuring spinal angulation, location of spinal angulation, spinal stiffness, rotation of an upper segment of the deformed vertebral column, rotation of a lower segment of the deformed vertebral column, height and weight of the subject,
   ii) based on parameters measured in said measuring step, calculating a distractive force necessary to correct the spinal angulation of the subject,
   iii) providing crutches to the subject, at least one of which comprises an actuator positioned at a distal end thereof,
   iv) having the subject assume a predator crouch position against a support while the subject engages and is braced by the crutches, and while the pelvis is tilted at a predetermined angle,
   v) straightening the deformed vertebral column by having the subject maintain the predator crouch position for a predetermined period of time during which a distractive force is transmitted from the actuator to a shoulder-girdle of the subject, thereby de-rotating a lower segment of the deformed vertebral column and de-rotating and axially lengthening an upper segment of the deformed vertebral column; and
   vi) repeating steps i) to v) at predetermined time intervals and over a period of time sufficient to treat the AIS.

2. The method of claim 1, wherein the predetermined angle is sufficient to cause de-rotation of the lower segment of the deformed vertebral column upon application of the distractive force.

3. The method of claim 1, wherein the step of straightening reduces the Cobb angle to 0°.

4. The method of claim 1, wherein the predetermined time intervals include daily.

5. The method of claim 1, wherein the spinal angulation is measured using one or more techniques selected from the group consisting of: radiography to measure a Cobb angle, scoliometer to assesa forward bend test, flexicurve spinal measurement and assessment via an external handheld computer assisted device.

6. The method of claim 1, wherein the predetermined angle ranges from 5° to 75°.

* * * * *